US006534014B1

(12) United States Patent
Mainquist et al.

(10) Patent No.: US 6,534,014 B1
(45) Date of Patent: Mar. 18, 2003

(54) SPECIMEN PLATE LID AND METHOD OF USING

(75) Inventors: James Kevin Mainquist, San Diego, CA (US); Robert Charles Downs, La Jolla, CA (US); Mark Richard Weselak, San Diego, CA (US); Andrew J. Meyer, San Diego, CA (US); Kristina Marie Burow, San Diego, CA (US); Daniel G. Sipes, Bethel Island, CA (US); Jeremy Caldwell, Del Mar, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 09/569,325

(22) Filed: May 11, 2000

(51) Int. Cl.[7] .................................................. C12M 1/22

(52) U.S. Cl. ...................... 422/99; 422/102; 435/288.4; 435/305.3

(58) Field of Search ................ 422/99, 102; 435/288.4, 435/305.3

(56) References Cited

U.S. PATENT DOCUMENTS 3,055,808 A * 9/1962 Henderson ............... 435/305.3
3,826,717 A * 7/1974 Gilbert
5,604,130 A * 2/1997 Warner et al.
5,863,792 A * 1/1999 Tyndorf et al.
6,051,423 A * 4/2000 Ceri et al.
6,254,833 B1 * 7/2001 Shumate et al.
6,258,325 B1 * 7/2001 Sanadi

OTHER PUBLICATIONS

"Well, Well, Wel . . . Greiner's 1536 Micro Assay Plates", The Scientist, vol. 12, 11, p. 15, (May 25, 1998.

* cited by examiner

*Primary Examiner*—Jan Ludlow
(74) *Attorney, Agent, or Firm*—Timothy L. Smith

(57) ABSTRACT

The specimen plate lid is generally a block, with a cover portion and a side portion. An alignment protrusion extends from the side portion and cooperates with an alignment member of the specimen plate to assist in manually or roboticly guiding the lid onto the specimen plate. An underside surface of the cover has a sealing perimeter for receiving a seal constructed from a compliant material, and shaped to cooperate with a complimentary sealing surface on the specimen plate. The lid is weighted so that when the lid is aligned and positioned on the specimen plate, the weight of the lid provides a gravitational force to sufficiently compress the seal against the sealing surface on the specimen plate. Accordingly, the lid is sufficiently sealed to the specimen plate to avoid contamination and impermissible drying.

34 Claims, 10 Drawing Sheets

SPECIMEN PLATE LID AND METHOD OF USING

FIELD OF THE INVENTION

The field of the present invention is the manufacture and use of lids for containers. More particularly, the present invention relates to lids for use on specimen plates, such as microplates.

BACKGROUND OF THE INVENTION

Specimen plates are used in several industries, such as the biotechnology and biomedical industries. The specimen plates can be used, for example, to hold multiple compounds or materials, to conduct multiple assays on one or more compounds, to facilitate high throughput screening and to accelerate the production and testing of a large number of samples. For the purpose of this discussion, the term “specimen” or “sample” refers to chemicals, assays, reagents, genetic material, biological compounds, or therapeutic material, in any form, such as a liquid, gel, or solid form.

Typically a specimen plate has multiple sample wells on its top surface into which one or more specimen can be placed, although a particular sample plate may have only a single well for the entire plate. Each of the wells forms a container into which a specimen is placed. The specimen plate also can be heated, cooled, or shaken to facilitate a desired process. Specimen plates are configured to meet industry standards. For example, some commonly used standard plates have 96, 384, or 1536 wells. Other sample plates are configured with 1, 2, 4, 6, 12, 24 or 48 wells. Such plates are available from, for example, Greiner America Corp., P.O. Box 953279, Lake Mary, Fla. 32795-3279. Plates may be handled manually or robotically.

It is known to use specimen plates in conjunction with automated processing equipment, such as high throughput screening equipment. Automated equipment, such as automated liquid dispensers, can receive appropriately configured specimen plates and deposit samples or reagents into the plate wells. Other known automated equipment facilitates the processing and testing of specimens using loaded specimen plates.

It is also known to provide a lid to cover a specimen plate. This is desirable in some applications. For example, the samples in the wells may need to incubate, or it may be desired to store the samples for an extended period of time. By covering the wells, contamination and evaporation may be reduced. Wells located near the edges of some known sample plates also can be prone to increased evaporation relative to middle wells when covered by a lid. This phenomena is often referred to as an “Edge Effect.” Such sample plates suffer a deficiency of non-uniform drying, which may cause inaccuracy in testing or assay procedures or other inefficiencies in automated processes.

It is known to cover a sample plate manually, such as by positioning a plastic lid over the top of the specimen plate. One such plastic lid is Model No. 656191 from Greiner America Corp., P.O. Box 953279, Lake Mary, Fla. 32795-3279. Such plastic lids suffer a deficiency in that it is difficult to form an air tight seal between the lid and specimen plate, leading to evaporation and the possibility of contamination. One known way to reduce those effects is to adhere tape around the edges of the plastic lid to seal the plastic lid to the plate. This makes access to the wells difficult in that the tape needs to be removed to gain access. In addition, adhesive residue can remain on the edges of the plate and lid, leading to the possibility of further contamination or difficulty in handling. Moreover, this covering and uncovering process is relatively time consuming and requires some manual dexterity. Substantial handling of the specimen plate is also required, which may undesirably agitate the contents of the wells and lead to inaccurate results. Alternatively, a foil tape can be applied directly to the top of the wells. Such foil tape also suffers from being time consuming to apply, increased contamination risk, and undue agitation.

Accordingly, there is a need for a specimen plate lid that provides enhanced sealing and provides increased efficiency in placement on a specimen plate or removal from a specimen plate. Further, there is a need for a specimen plate with improved gas exchange characteristics.

SUMMARY OF THE INVENTION

The present invention alleviates to a great extent the disadvantages of the known specimen plate lids and methods of using them by providing a specimen plate lid having a seal between a lower surface of the lid and a mating upper surface of a specimen plate. Generally, the lid includes a plate member having an exterior surface that is exposed when placed on a specimen plate, and an lower/inner surface that faces the specimen plate when placed on top of the specimen plate. Preferably a side portion extends from the periphery of the lower/inner surface so that the side portion overlaps with side surfaces of the specimen plate when the lid is placed over the specimen plate. The side portion has an exterior surface that is exposed and an inner surface facing the specimen plate when the lid is placed over the specimen plate.

Alignment tabs preferably are located on the side portion and cooperative mating elements are located on the specimen plate to assist in guiding the lid onto the specimen plate and in providing a desired registration with the specimen plate. The lower surface of the lid has a sealing perimeter constructed to cooperate with a complementary sealing surface on the specimen plate. A seal formed from a compliant sealing material is positioned between the lower surface of the lid and the specimen plate. The seal is shaped to cooperate with both the sealing perimeter on the lid and the complementary sealing surface on the specimen plate. Preferably seal retaining members are provided on the sealing perimeter of the lid to retain the seal in place. The lid also preferably has sufficient weight to compress the seal when the lid is aligned and positioned on the specimen plate. In this way, the weight of the lid provides a gravitational force sufficient to compress the seal against the sealing surface on the specimen plate, enhancing the level of diffusion resistance.

It is an advantage of the present invention that the specimen plate lid can be accurately and relatively efficiently positioned on a specimen plate. Since the lid and its compressible seal alone provide a good barrier between the specimen plate wells and the outside environment, additional mechanical or adhesive sealing is not required. This saves material and also can reduce the time required to cover and seal a specimen plate. Moreover, agitation and other disturbance of the specimen material in the wells can be minimized.

It is a further advantage that the specimen plate lid is well suited for handling by a robotic material handling system. For example, the lid is generally self-aligning, permitting the lid to be easily positioned by robotic handling. Additionally, since the lid is self-sealing with the specimen plate, operator intervention is not required to mechanically seal the plate.

These and other features and advantages of the present invention will be appreciated from review of the following detailed description of the invention, along with the accompanying figures in which like reference numerals refer to like parts throughout.

DETAILED DESCRIPTION OF THE INVENTION

Figure 1:
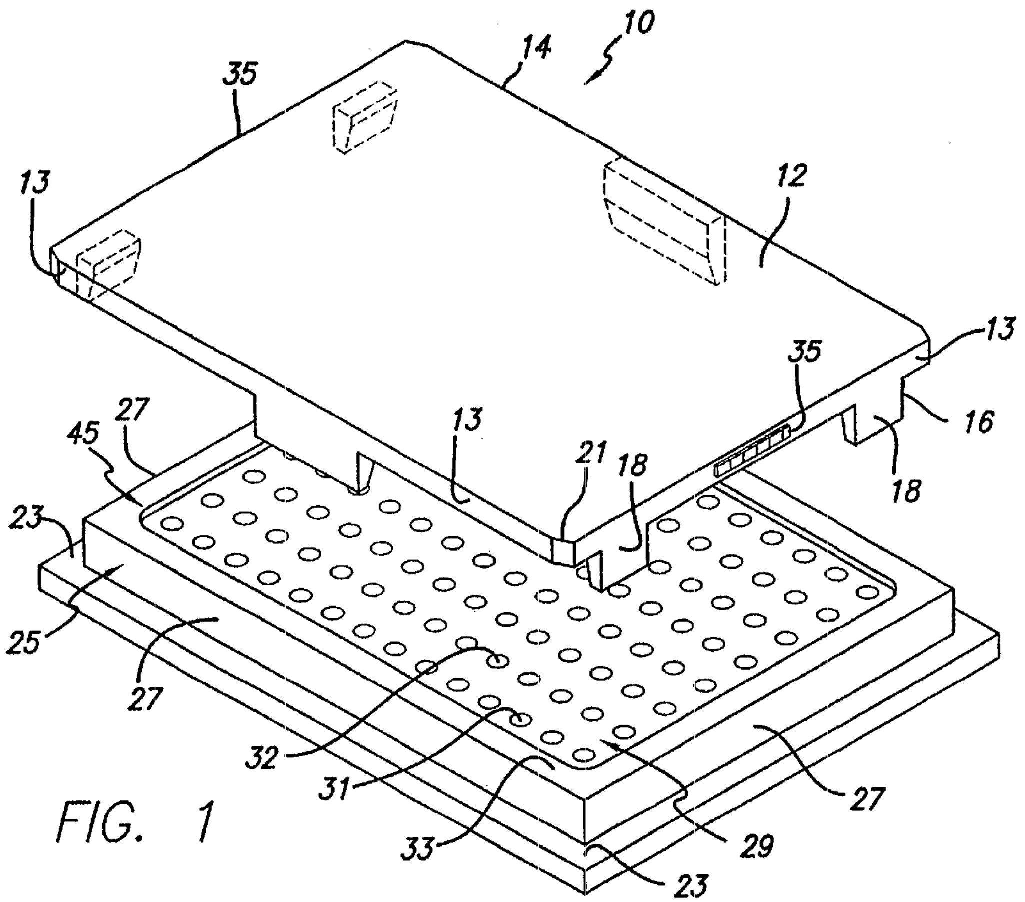
FIG. 1 is a perspective view of a specimen plate lid and specimen plate in accordance with the present invention.

In accordance with the present invention, a specimen plate lid is provided. Referring now to FIGS. 1–7, there is shown a specimen plate lid 10 made in accordance with the present invention. Specimen plate lid 10 is generally a block having a cover portion 12 and side portions 13. The cover 12 has an x-axis edges 14 and a y-axis edges 16. An alignment protrusion in the form of two alignment tabs, or legs, 18 are positioned along each y-axis edge 16 while one x-axis alignment tab, or leg, 19 is positioned on each x-axis edge 14. It will be appreciated that other numbers and positions of alignment tabs can be used depending upon the size and shape of the specimen plate. Further, it will be appreciated that the alignment protrusion can take alternative forms, such as a lip, pins, a curtain, or comer tabs.

The y-axis alignment tabs 18 are positioned spaced apart and near the ends of each y-axis edge 16. Each x-axis alignment tab 19 is positioned approximately centered on each corresponding x-axis edge 14. It will be appreciated that the alignment tabs may be positioned at different locations adjacent the edges of the specimen plate lid 10.

The specimen plate 25 is also generally a block having a sample area 29 and sidewalls 27. The sample area 29 includes many sample wells such as exterior well 31 and interior well 32. A perimeter surface 33 is positioned at the top of the sidewalls 27 and surrounds the sample area 29. It will be appreciated that although the surface area 33 is shown as substantially a rectangular frame, other shapes and geometries are contemplated. At the bottom edge of sidewall 27 is a registration edge 23. Registration edge 23 facilitates the efficient positioning in automated equipment.

In use, the specimen plate lid is placed on the specimen plate 25 to cover and sufficiently seal the wells. To facilitate the gentle and efficient covering and uncovering of the specimen plate, the alignment tabs on lid do not frictionally mate with the sidewalls of the specimen plate. Instead, the alignment tabs are constructed to cooperate with the sidewalls of the plate and to guide the lid to the specimen plate, but have sufficient spacing so that the tabs do not frictionally engage the sidewalls of the specimen plate.

To precisely position the lid, the alignment tabs are constructed with a tolerance of about 0.13 mm. It will be appreciated that other tolerances can be used to precisely place the lid on the specimen plate. Such precise positioning permits the seal to be compressed without the seal touching any sample well.

To cover the sample area of the specimen plate, the lid 10 is lifted and positioned above the sample area 29 of the specimen plate 25. It will be appreciated that the lifting and positioning may be performed manually or by a machine such as a robot. The specimen plate lid 10 is generally aligned with the specimen plate 25 and lowered. As the cover 12 is lowered, the alignment tabs 18, 19 begin to cooperate with the sidewalls 27 on the specimen plate. Optionally, each of the alignment tabs 18, 19 has a chamfer 39 at its lower portion to facilitate self-aligning the lid 10 to the plate 25. With the alignment tabs chamfered, the alignment tabs more readily engage the sidewalls of the plate, but accurately position the lid as the lid is lowered. In such a manner, the cover 12 can be only approximately positioned above the sample area 29 and as the cover 12 is lowered, the chamfered alignment tabs 18, 19 guide and align the cover 12. Thereby, when the cover 12 is fully resting on the specimen plate, the cover 12 is precisely positioned and aligned with the specimen plate 25.

Figure 2:
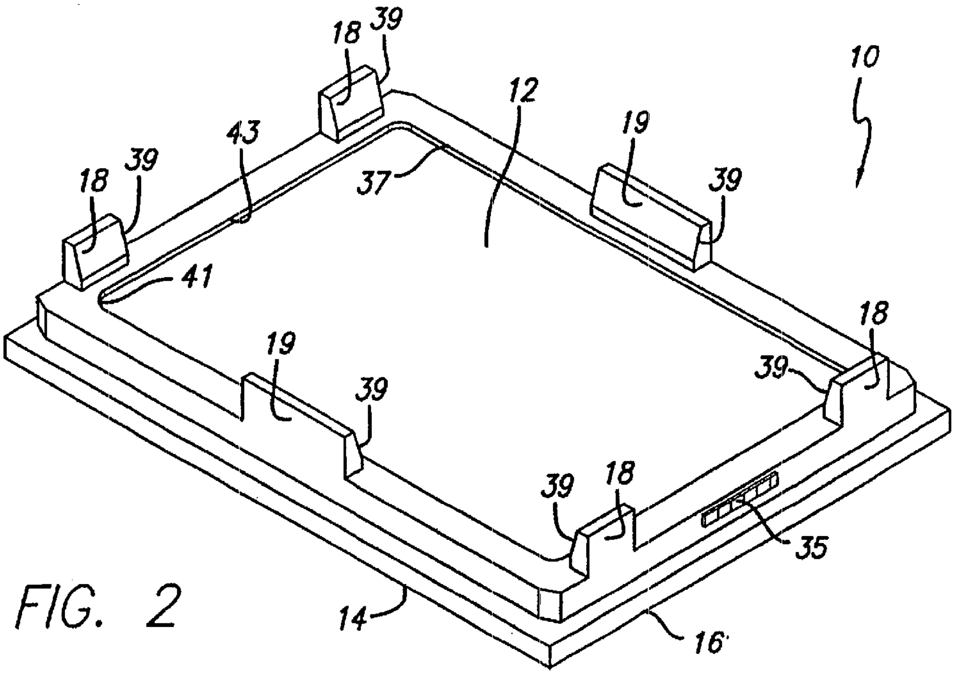
FIG. 2 is a perspective view of an inner surface of a specimen plate lid in accordance with the present invention.
Figure 3:
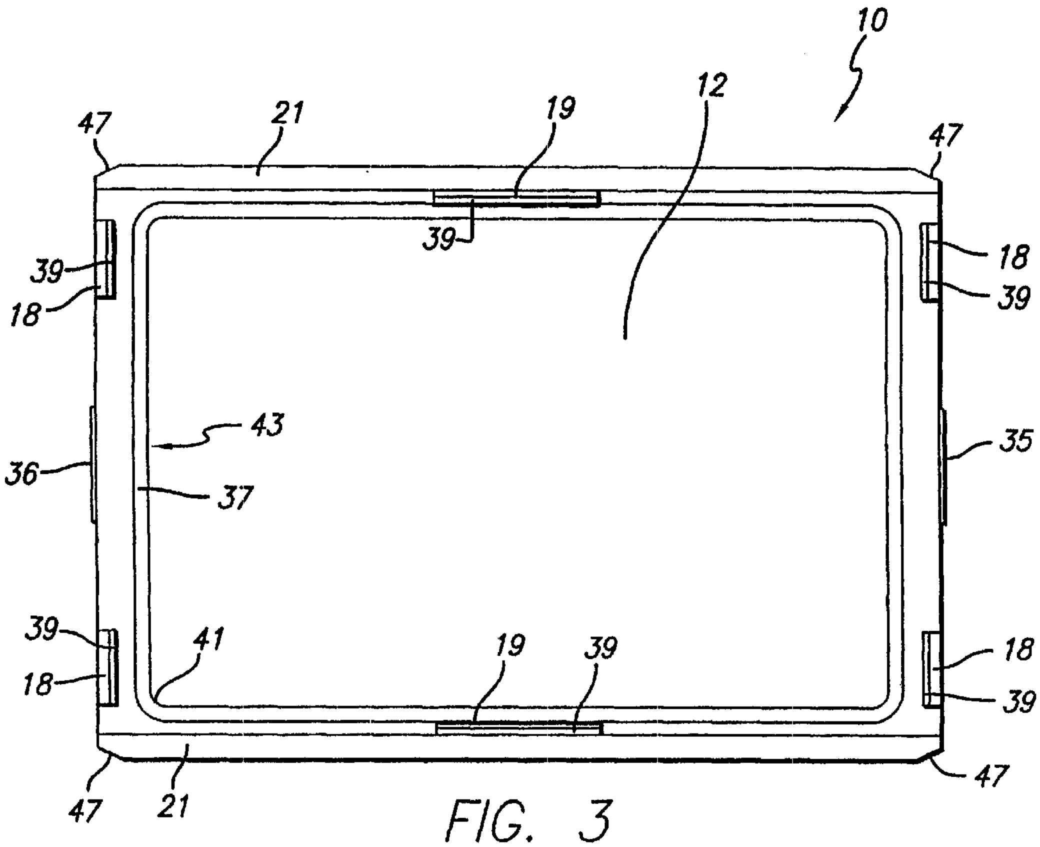
FIG. 3 is a bottom plan view of a specimen plate lid in accordance with the present invention.
Figure 4:
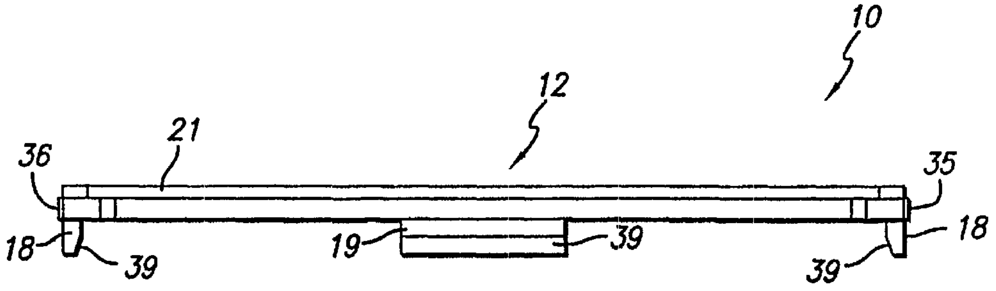
FIG. 4 is a side view of a specimen plate lid in accordance with the present invention.
Figure 5:
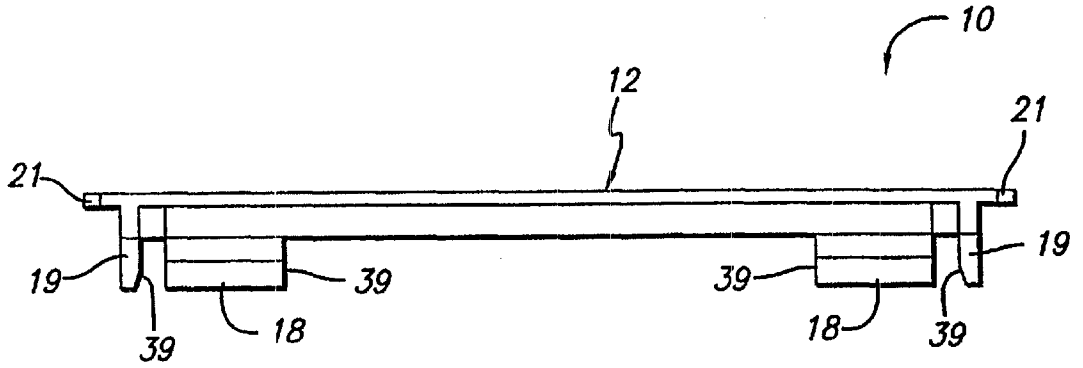
FIG. 5 is another side view of a specimen plate lid in accordance with the present invention.
Figure 6:
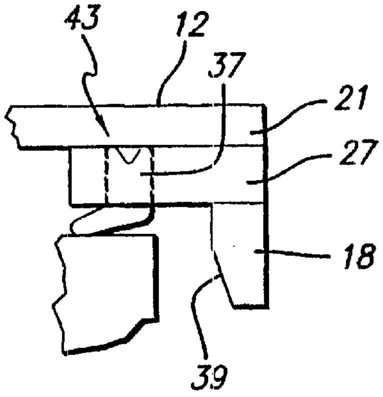
FIG. 6 is a fragmentary side view of a portion of a specimen plate lid in accordance with the present invention.
Figure 7:
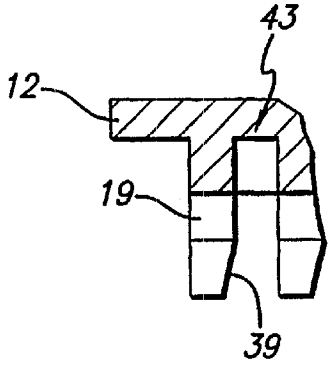
FIG. 7 is a fragmentary side view of a portion of a specimen plate lid in accordance with the present invention.

Referring now to FIG. 2 the underside of cover 12 is shown to have a sealing perimeter constructed as a groove 43 adjacent the perimeter of the cover 12. The groove 43 provides a sealing area on the lid and is positioned such that when the cover 12 is positioned on the specimen plate 25, the groove 43 aligns approximately in the center of the perimeter surface 33 of the specimen plate 25. It will be appreciated that a sealing area may be provided on the lid in other ways, such as providing a flat surface for adhering a seal. It will also be appreciated that the seal could be attached to the specimen plate and positioned to cooperate with a sealing perimeter on the lid.

In the disclosed example, a rubber seal 37 is fittingly retained in the groove 43. It will be appreciated that other methods such as adhering may be used to fix the seal 37 in the groove 43. However, a frictional fit is preferred as the seal 37 may be conveniently removed for cleaning, replacement, or sterilization. The seal 37 is preferably a rubber, and most preferably a silicon rubber. Silicon rubber, or another highly compliant material, is preferred as an efficient seal can be created with a minimum compressive force.

With the seal 37 constructed from a highly compliant material and fittingly positioned in the groove 43, when the cover 12 is fit onto the specimen plate 25, the seal 37 is compressed by the weight of the lid to the perimeter surface 33. The perimeter surface 33 is a sealing surface for compressibly receiving the seal 37.

In a preferred configuration, the specimen plate lid 10 is constructed as a single piece machined from a stainless steel block. Stainless steel is a preferred material as not only does stainless steel have superior sterilization characteristics, but stainless steel is also a heavy material. By constructing the specimen plate lid 10 from a heavy material, sufficient gravitational forces act to compress the cover 12 towards the specimen plate 25. In such a manner the seal 37 is sufficiently compressed to the sealing surface 33 to create a seal that provides a barrier against contamination and evaporation. Those skilled in the art will recognize that the specimen plate lid 10 can be weighted using other means, such as adding weights to the over 12 or tabs 18, 19 or constructing the lid 10 from an alternate heavy material. To sufficiently compress the compliant seal, preferably the lid weighs between about 100 grams and about 500 grams. Most preferably, the lid weighs about 400 grams. It will be appreciated that the disclosed weight range is for a standard size specimen plate using a silicon rubber seal. Other weights may be used for other size plates and other compliant seals. Further, some applications may not require such complete sealing and may sufficiently seal with less weight.

Stainless steel is also a preferred material because of its superior machining characteristics. Due to the geometry and narrowness of the perimeter surface 33, it is important that the cover 12 be accurately positioned and aligned with the specimen plate 25. By machining the alignment tabs 18, 19, the tabs can be accurately located to within 0.100 millimeter tolerance. Further, for efficient sealing, the underside of the cover 12 needs to be substantially flat. Again, by machining, flatness can be assured to within 0.100 millimeter tolerance. Although the preferred example machines the specimen plate lid from a solid block of stainless steel, it will be appreciated that a stainless steel piece could be cast roughly in the shape of the specimen plate lid, and then selected surfaces machined as required. Further, it will be appreciated that other materials could be substituted, such as aluminum. Although the described example uses a lid formed from a single block, it will be appreciated that the lid may be constructed from component parts.

Optionally, the specimen plate lid 10 may include a bar code 35 positioned at one end, and a bar code 36 placed at the other end. The indicia on each bar code 35, 36 identifies the particular specimen plate lid, but each bar codes has an indicia that facilities identifying which end of the lid is being scanned. For example, bar code 35 may be an even code while bar code 36 is an odd code. Therefore, an automated machine can read the bar code 35, 36 and know whether a front end or a rear end of the lid is being inserted into the machine. In a similar manner, bar codes can be positioned on the specimen plate 25 to identify which end of the specimen plate is being inserted into a machine. If both the lid and the specimen plate have bar codes, then the system can assure that the lid is positioned in the same orientation on the specimen plate.

The specimen plate lid 10 may be used as described for manual use. In such a manner, a technician or other operator manually grabs, aligns, and lowers the specimen plate lid 10 over the specimen plate 25. In a similar manner, the technician or user would remove the specimen plate lid 10. However, it may be desirable for some applications that the specimen plate lid 10 be fitted and removed by an automatic system, such as a robotic system. To facilitate manipulation by an automatic robotic system, the specimen plate lid 10 can optionally include a gripper lip 21 on the x-axis edges 14. It will be appreciated that other structures may be positioned on the specimen plate lid 10 for cooperating with a gripper mechanism on a robotic system.

In use by robotic system, first a gripper portion of a robotic member would cooperate or couple with one or both gripper lips 21. The robotic member would then approximately position the specimen plate lid 10 above the sample area 29. The robotic member would lower the cover 12 until the alignment tabs 18, 19 begin contacting the sidewalls 27 of the specimen plate 25. As the cover 12 is lowered, the robotic member preferably allows the cover 12 to adjust and self-align to the sidewalls 27 of the specimen plate 25. After the cover 12 is fully lowered, the gripper portion of the robotic member can release the gripper lips 21 and the robotic member can be retracted. The robotic member may also include a bar code reader for reading bar code 35, 36 for identifying the lid or specimen plate, and determining which side of the lid or plate is leading.

Figure 8:
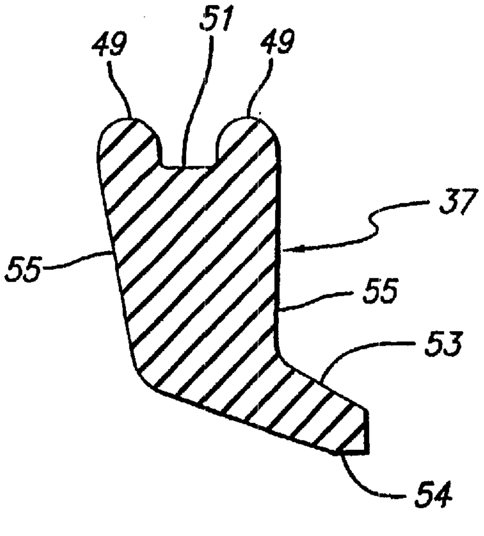
FIG. 8 is a cross-sectional view of an example of a compliant seal in accordance with the present invention.
Figure 9:
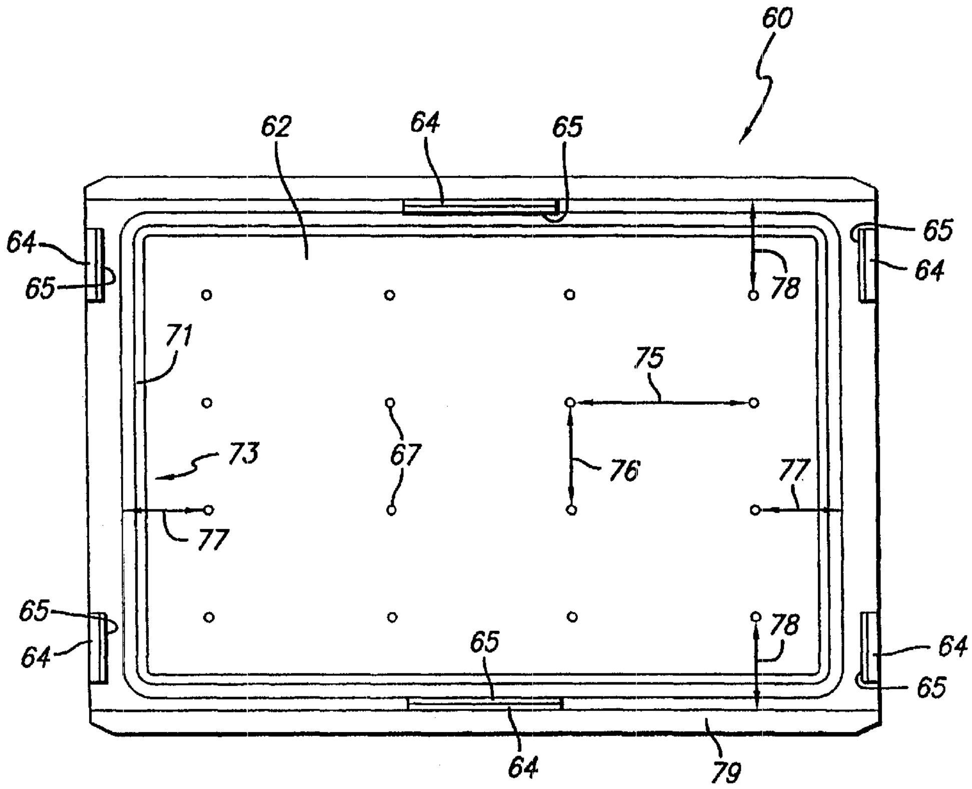
FIG. 9 is a bottom plan view of an alternative embodiment of a specimen plate lid in accordance with the present invention.
Figure 10:
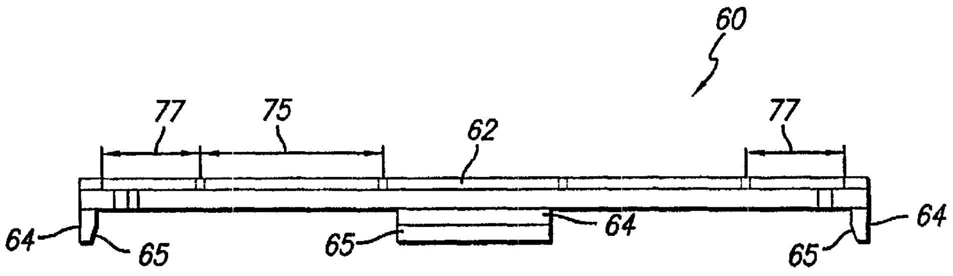
FIG. 10 is a side view of the specimen plate illustrated in FIG. 9.
Figure 11:
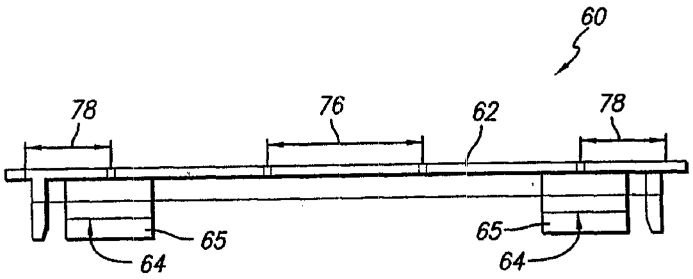
FIG. 11 is another side view of the specimen plate lid illustrated in FIG. 9.

Referring now to FIG. 8, a seal 37 is shown for use on the lid 10. The seal 37 has sidewalls 55 which are fittingly received into the groove 43. The seal 37 has two ridges 49 and a recess 51 configured to more evenly distribute a load received on the seal 37. The seal 37 also has a lip 53 which extends over the perimeter surface 33. Therefore, as the lid 10 is lowered onto the specimen plate 25, the load-bearing surface 54 contacts the perimeter surface 33 and is compressed thereto as the lid is fully lowered.

In the described example of the specimen plate 25, the sample area 29 is substantially planer with the perimeter surface 33. Therefore, a minimum volume of air 45, or other gas, is retained between the cover 12 and the sample area 29 when the lid is resting on the plate. The volume 45 of gas retained is directly proportional to the thickness of the seal 37, and more particularly on the thickness of the lip 53. Therefore, by minimizing the thickness of lip 53, the volume of air or other gas entrapped as a volume when the lid is in place is minimized.

Such a minimum volume of retained gas is desired in some applications as moisture from within the wells can be evaporated into the retained volume 45. For example, if the samples are to be stored for an extended period, it may be desirable to reduce evaporation. By reducing the retained volume 45, drying effects are minimized. Such drying effects can be particularly severe in the exterior wells such as exterior well 31 that are near the outside perimeter of the sample area 29.

Although a particular geometry has been shown for seal 37, it will be appreciated that other seals constructed from a highly compliant material can be substituted. Further, it will be appreciated that other shapes, with or without a lip, can be used to provide a sufficient seal between the cover 12 and the specimen plate 25. Further, the geometry and shape of the perimeter area 33 or other sealing area may direct modification in the seal shape and geometry.

Referring to FIGS. 9–13, another example of a specimen plate lid 60 is shown. Specimen late lid 60 is similar to specimen plate lid 10, with the similar aspects only briefly addressed. Specimen plate lid 60 has a cover 62 and sidewalls, with an alignment protrusion constructed as alignment tabs 64 extending therefrom. As with alignment tabs 18, 19 alignment tabs 64 have a chamfer 65 for facilitating efficient alignment and positioning. Cover 62 optionally has a gripper lip 79 for cooperating with a robotic member.

Specimen plate lid 60 is constructed such that when the specimen plate lid 60 is resting on a corresponding specimen plate, a more substantial volume 83 of gas is retained between the cover 62 and the sample area of the specimen plate. Such a substantial volume 83 of gas is desirable, for example in an assay specimen plate. In an assay specimen plate, it is desired that gas in the volume space 83 interact with the wells in the specimen plate. The wells may contain, for example, live cells that need oxygen, humidity, N2, and CO2 to survive. However, it is important that the gases interact with the wells in a uniform and consistent manner. Such uniformity and consistency is difficult to achieve as the wells have different evaporative characteristics closer to the perimeter than the wells more towards the center of the sample area.

In some applications, it is desired that outside gases diffuse and mix with the gases in the retained volume 83. Accordingly, the cover 62 of the assay plate lid 60 may be provided with a series of small holes 67. In a preferred embodiment, each hole 67 is approximately 1 millimeter in diameter. It will be appreciated that other sized holes may be substituted depending upon specific applications. Also, in the disclosed example 16 holes are positioned in a grid pattern such that each hole is placed an x-axis distance 75 from an adjacent hole and a y-axis distance 76 from an adjacent hole. The x-axis edge distance 77 is substantially the same from each outer hole to the x-axis edge, and the y-axis edge distance 78 is substantially the same from the outside holes to the y-axis edge. It will be appreciated that other numbers and spacings of holes may be used. Alternatively, the cover can be constructed with a semi-permeable gas membrane in an opening. The membrane can be a single pane, or can be constructed in multiple panes in multiple openings arranged in the cover. By selecting the membrane's pemeability, size and placement, the gas difference characteristic of the assay lid can be adjusted.

Even though the cover 62 has through-holes permitting the diffusion of gas into the volume area 83, it has been found to be desirable that the cover 62 still be constructed to sufficiently seal to the specimen plate 25. Without such sealing, the wells near the perimeter of the sample area are found to impermissibly dry due to excess evaporation, and gas diffusion to the exterior wells is not uniform. Accordingly, the underside of cover 62 has a groove 73 and a seal 71 similar to the groove and seal already discussed.

In use, the assay plate lid 60 is fittingly positioned on a specimen plate, and the lid and plate assembly typically placed in an enclosed chamber. The enclosed chamber contains a desirable gas or a gaseous mixture. For example, the chamber may be filled with oxygen. With the lid and plate assembly in the chamber, the oxygen enters the volume 83 and mixes with the gas in the chamber 83 and diffuse and react with substances in the well of the plate.

Even though it is sometimes desirable that the ambient gas mix with the gas in the volume 83 and react with the material in the well, it is also desirable that the material in the well not impermissibly dry. For example, each time the lid is fitted to the specimen plate, the moisture or solvent in each well evaporates until the moisture in the volume 83 establishes an equilibrium. Therefore, the gas exchanged with the ambient gas must be carefully controlled to avoid impermissible drying. Accordingly, the size and spacing of the through-holes is selected to control gas diffusion and drying effects.

Figure 12:
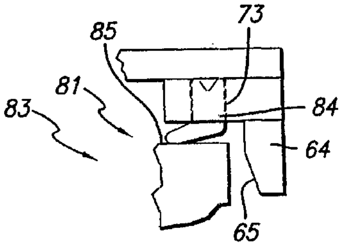
FIG. 12 is a fragmentary side view of a portion of the specimen plate lid illustrated in FIG. 9.
Figure 13:
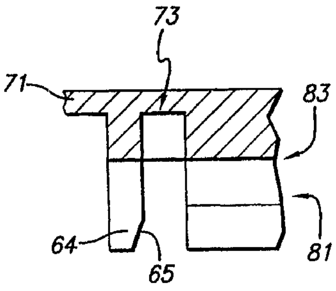
FIG. 13 is a fragmentary side view of another portion of the specimen plate lid illustrated in FIG. 9.

Referring now to FIG. 12, the volume 83 is obtained by providing a recess 81 in the underside of the cover 62. Accordingly, the size of the recess 81 is directly proportional to the retained volume of gas 83. In a preferred embodiment, the recess 81 is machined from the solid stainless steel block comprising the lid 60. It will be appreciated that other methods of obtaining the recess may be used. A ridge 85 remains between the groove 73 and the recess 81. The ridge 85 supports the seal lip 84 of the seal 71 when the seal 71 is compressed against the perimeter area on the specimen plate.

Figure 14:
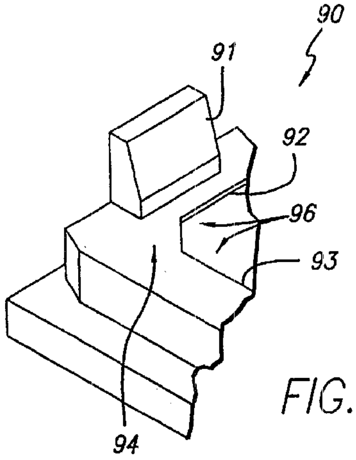
FIG. 14 is a fragmentary perspective view of a specimen plate lid in accordance with the present invention.
Figure 15:
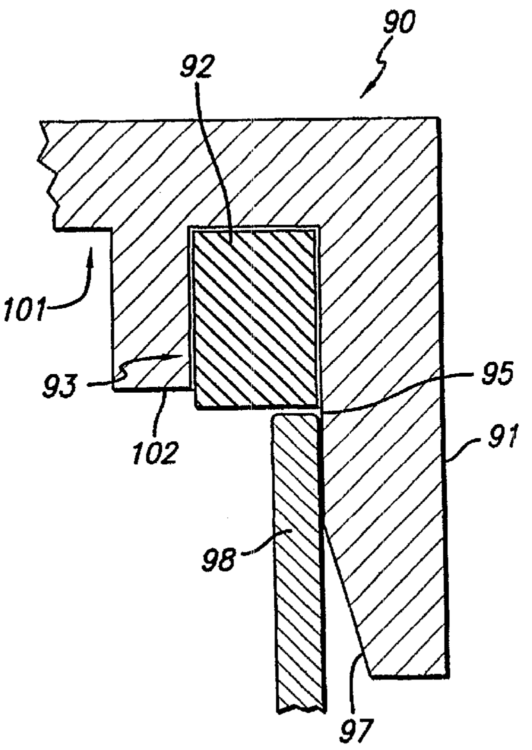
FIG. 15 is a cross-sectional view of a groove and seal in a specimen plate lid in accordance with the present invention, with a sealing surface of the specimen plate positioned near an edge of the seal.
Figure 16:
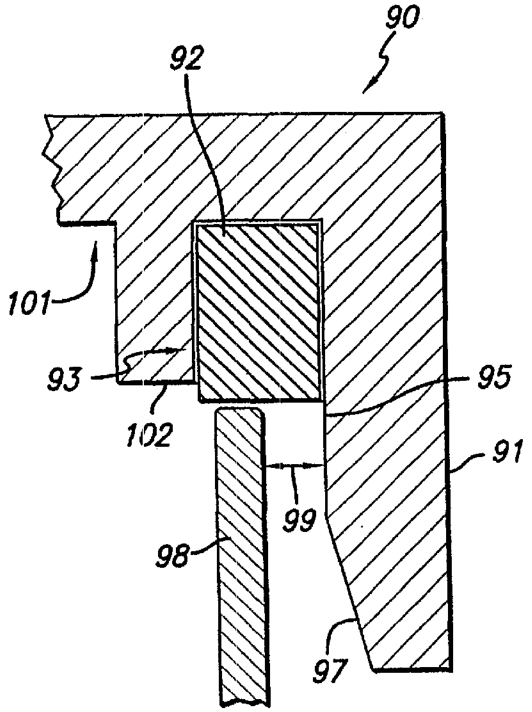
FIG. 16 shows the lid of FIG. 15 with the sealing surface of the specimen plate positioned near the center of the seal.

The specimen plates described thus far have a perimeter area functioning as a sealing area for compressibly receiving a seal. However, other available specimen plates do not provide a perimeter surface, but instead provide a more narrow plate sidewall 98 as shown in FIGS. 14–16. In such a manner, a soft compliant seal 92 compressibly receives a top surface of the plate sidewall 98. Accordingly, the top surface of sidewall functions as a sealing surface. The seal 92 is most preferably constructed of a silicon rubber, but other highly compliant materials could be substituted. The seal 92 is fittingly received into a groove 93. Due to tolerances in the lid 90 or the positioning of the plate sidewall 98, the plate sidewall 98 may not always be received at the same position in the seal 92. For example, FIG. 16 shows that the top surface of the plate sidewall 98 may be received near the center of the seal 92, whereas in FIG. 15 the top surface of the plate sidewall 98 is received at an outer edge of the seal 92.

Specimen plate lid 90 has alignment tabs or legs 91, each having a chamfer surface 97. The chamfer surface 97 assists in aligning the plate sidewall 98 with the seal 92. The specimen plate lid 90 is an assay plate lid having a volume 101 of gas retained beneath the lid. As with plate lid 60 described above, specimen plate lid 90 has a ridge 102. The ridge 102 provides lateral support to the seal 92.

FIG. 14 shows an example comer construction for the specimen plate lid 90. For particular specimen plates, the plate sidewall 98 may be constructed to traverse corners using two 45-degree angles instead of a single 90-degree corner. Such a corner configuration is not only efficient to manufacture, but provides superior support as compared to a 90-degree angle. Since the plate sidewall 98 is narrow, the groove 93 in the cover 94 also needs to extend across corners using two 45-degree angles 96. In such a manner the plate sidewall 98 more accurately cooperates with the seal 92.

Figure 17:
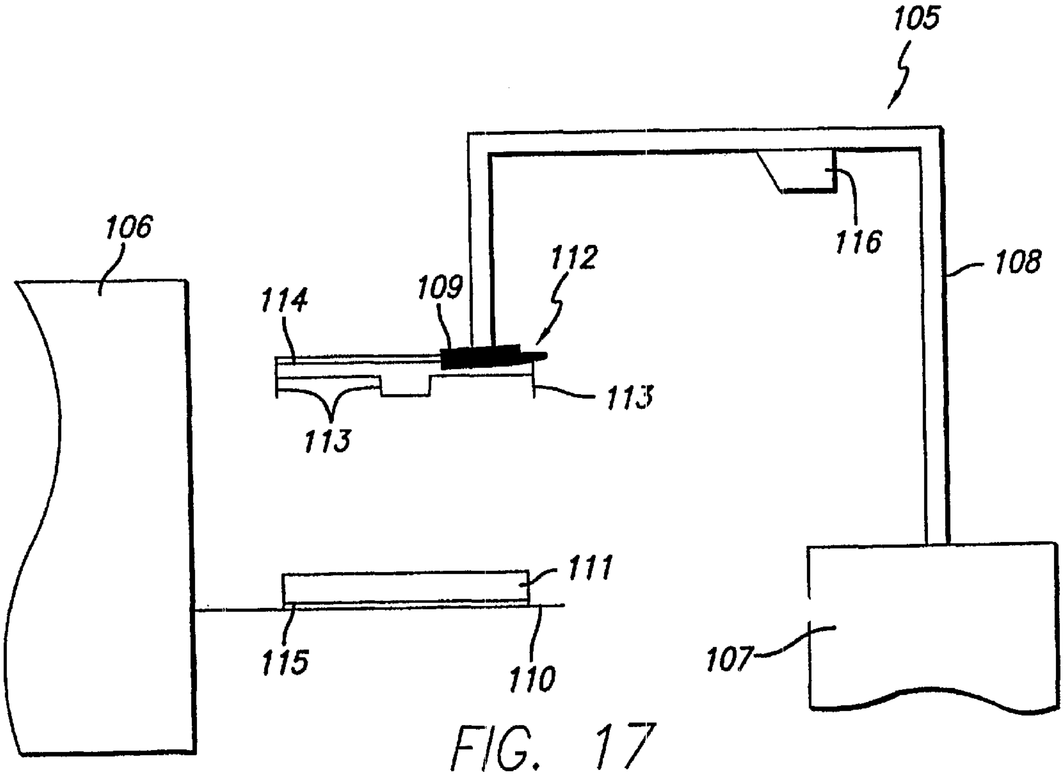
FIG. 17 illustrates an example of a robotic transport system and a specimen plate lid in accordance with the present invention.

Referring now to FIG. 17, a robotic system 105 is shown operating in accordance with the present invention. The robotic system 105 has a robot 107 with a robotic arm 108. A gripper attachment 109 is positioned at the end of the robotic arm 108. The robotic system also includes one or more work stations, such as workstation 106. The workstation may be, for example, a holding station, a shaker station, an optical reader station, or an automated dispensing station.

The workstation 106 has a holding area 110. Both the workstation 106 and the gripper attachment 109 of the robot 107 have access to the holding area 110. A specimen plate 111 is shown in an uncovered arrangement in FIG. 17. The specimen plate has a registration lip 115 that assists in positioning the specimen plate with the workstation 106. Alternatively, the registration lip 115 may be configured to couple with the gripper attachment so that the robot can move and position the plate 111.

The specimen plate 112 lid has a gripper attachment structure in the form of a pair of gripper lips 114 positioned on each of the lid's x-axis edges. The robotic gripper attachment 109 is configured to removeably couple with the gripper lips 114. In such a manner, the robot 107 is able to couple with the lid 112, and lift and position the lid according to the needs of an automated process. It will be appreciated that other gripper attachment structures can be used according to application requirements.

The specimen plate lid 112 also has an alignment protrusion in the form of alignment tabs 113 for cooperating with sidewalls of the plate 111. As the robotic arm 108 lowers the lid 112, the tabs 113 begin to engage the sidewalls. As the robot 107 further lowers the lid, the robotic arm 108 and gripper attachment 109 permit the lid to self-align with the plate 111. When the lid is fully resting on the plate 111, the gripper attachment disengages and the robotic arm 108 moves away from the workstation 106. Optionally, the robotic system can include a barcode reader 116 for reading a barcode on the lid or the plate for properly identifying plates or lids. Although the barcode reader 116 is shown on the robotic arm, it will be appreciated that the barcode reader can be placed in other locations.

Figure 18:
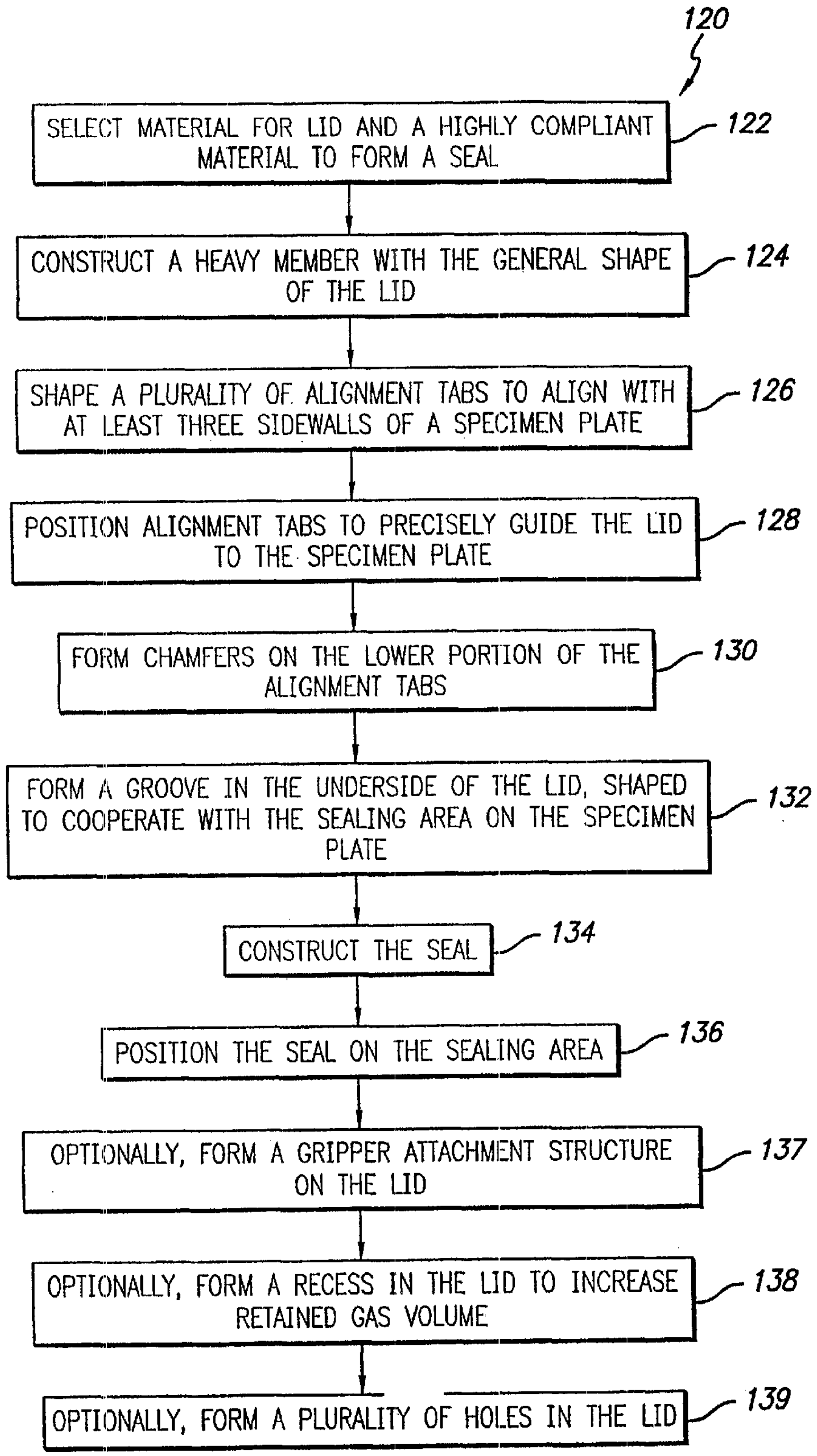
FIG. 18 is a flowchart of a method of manufacturing a specimen plate lid in accordance with the present invention.

Referring now to FIG. 18, a method of manufacturing 120 a specimen plate lid is shown in accordance with the present invention. Block 120 shows that an initial step is to select the proper material for the lid and the proper material for the seal. As described above, the lid is preferably made from a stainless steel block. However, it will be appreciated that other materials or constructions can be used to provide sufficient weight. Further, it will be understood that a lighter material can be selected and weights added to the lid during construction. As already described, the seal is preferably constructed from a highly compliant rubber such as a silicon rubber. However, it will be appreciated that other materials can be substituted.

The block is preferably formed into the general shape of the lid by machining as shown in block 124. However, it will be appreciated that the member can be generally shaped using other methods such as casting. Alignment tabs, or legs, are positioned on the lid such that the alignment tabs will align and cooperate with at least three sidewalls of a specimen plate as shown in block 126. The tabs are preferably formed with a tolerance in the range of about 0.100 mm to about 0.2 mm, thus providing an accurate positioning of the lid on the specimen plate. Accordingly, the seal will not contact any wells on the sample plate. It will be understood that the number and position of the alignment protrusion or alignment tabs may be adjusted according to specific applications.

In block 128 the tabs are precisely positioned on the lid to guide the lid to the specimen plate. In a disclosed example, such precise positioning is accomplished by machining the alignment tabs. It will be appreciated that other methods can be used to attach and position the alignment tabs. Chamfers are formed on the lower portion of the alignment tabs as shown in block 130. The chamfers facilitate self-aligning the lid to the specimen plate.

A groove is formed on the underside of the lid as shown in block 132. The groove is shaped and has a geometry that cooperates with a sealing area on the specimen plate. The sealing area the specimen plate may be, for example, a surface area or may be a plate edge. It will be appreciated that depending upon the specific specimen plate to be mated with, the sealing area may be shaped to precisely mate with the sealing surface on the specimen plate or may accommodate greater tolerances.

Block 134 shows that the seal is constructed from a highly compliant material, and in block 136 the seal is positioned on the sealing area. It will be appreciated that the sealing area may include a groove for fittingly receiving the seal, or the seal may be attached to the sealing area using another method.

Block 137 shows that a gripper attachment structure optionally may be formed on the lid. For example, the gripper attachment structure may be a gripper lip for coupling with a gripper attachment on a robotic arm. In Block 138 an optional recess may be formed in the lid to increase the volume of the retaining gas when the lid is in place on the specimen plate. In such a manner, the lid functions as an assay lid. In the preferred embodiment, the recess is formed by machining the stainless steel block. However, it will be appreciated that the recess may be formed using other methods.

Optionally, as shown in block 139, a plurality of holes may be formed in the lid. It will be appreciated that the size and specific location of the holes may be adjusted for specific applications. As described earlier, the holes function to allow gas to diffuse into the retained gas volume.

Figure 19:
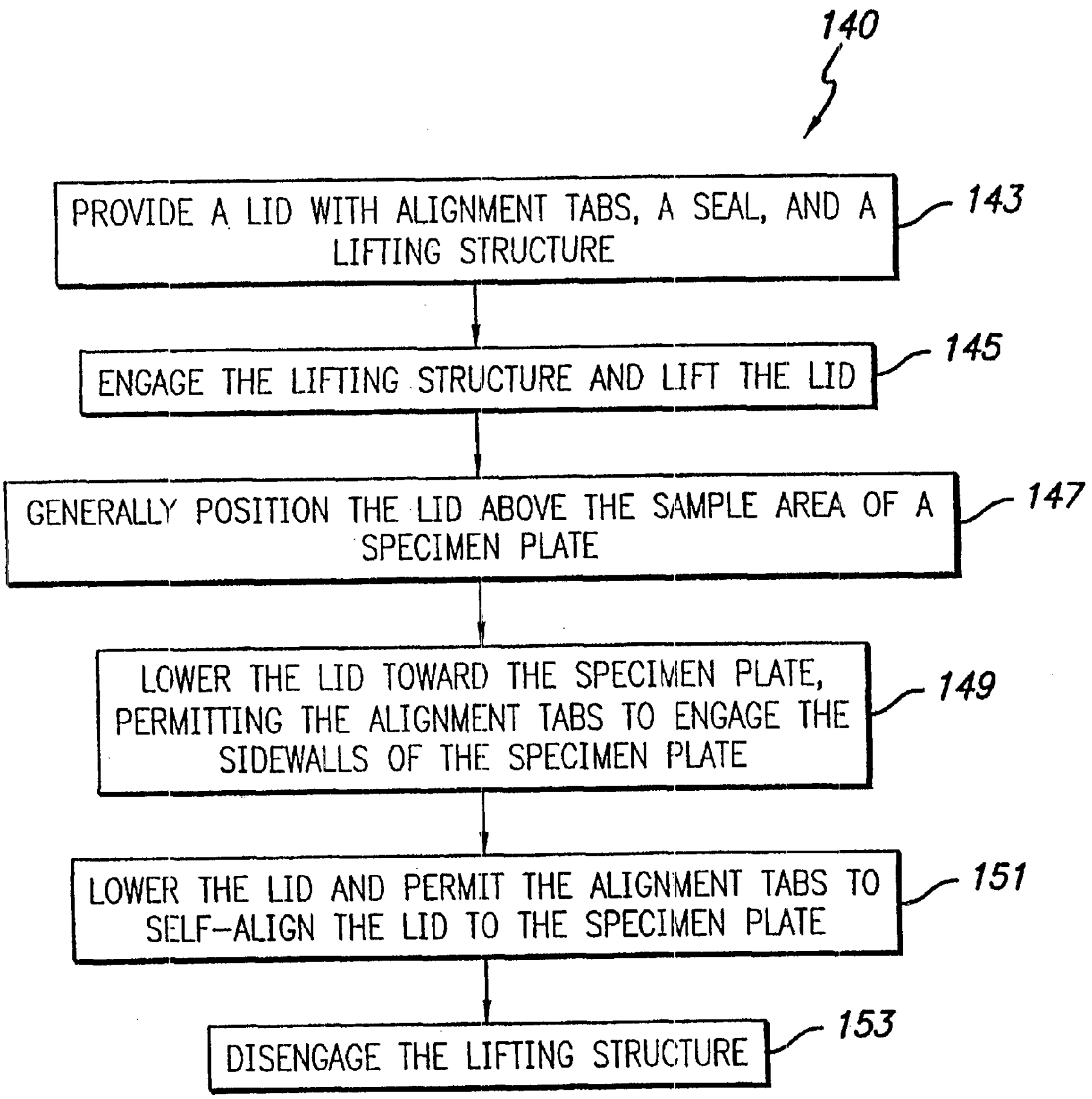
FIG. 19 is a flowchart of a method of using a specimen place lid made in accordance with the present invention.

Referring now to FIG. 19, a method of using 140 a specimen plate is shown in accordance with the present invention. Block 143 provides a lid with alignment tabs, a seal, and a lifting structure. In block 145, the lifting structure is engaged to lift the lid. The lid is then generally positioned above the sample area of the sample plate as shown in block 147. In block 149, the lid is partially lowered toward the specimen plate, thereby permitting the alignment tabs to begin to cooperate and engage the sidewalls on the specimen plate. As the lid is further lowered, the alignment tabs adjust the position of the lid to self-align the lid to the specimen plate as shown in block 151. Once the lid is resting on the specimen plate, the lifting structure is disengaged as shown in block 153.

The lid may be constructed to be lifted and fitted either manually or by robotic means. Accordingly, the lid may include lifting structures for mating with a gripper portion of a robotic system, such as a gripper arm. The lid may therefore have a gripper structure such as a gripper lip as described earlier. It will be appreciated that other types of gripper structures may be provided on the lid depending on specific application.

Figure 20:
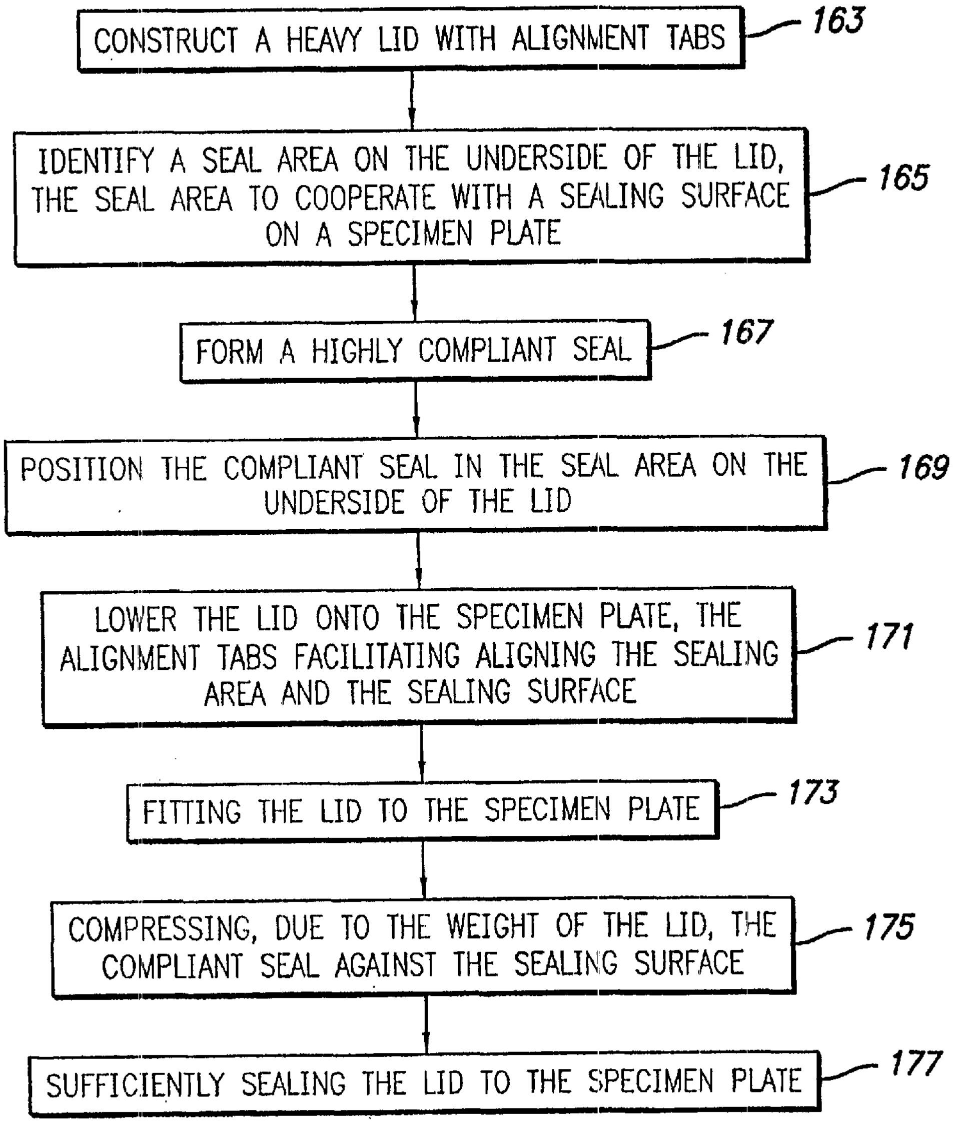
FIG. 20 is a flowchart of a method of manufacturing and using a specimen plate lid in accordance with the present invention.

Referring now to FIG. 20, a method of sealing 160 a specimen plate is shown. Block 163 shows that a lid is constructed to be heavy and with alignment tabs extending from the lid. In block 165, a sealing area is identified on the underside of the lid. The sealing area is selected to cooperate with a sealing surface on a specimen plate. For example, the sealing surface on the specimen plate may be a flat sealing area, or may be a plate edge as described earlier. It will be appreciated that the sealing area may be selected with varying geometries and positions according to specific applications.

In block 167, a seal is constructed from a highly compliant material. As described earlier, the highly compliant material may be a rubber material such as a silicon rubber or plastic. It will be appreciated that other materials can be substituted. The compliant seal is positioned in the seal area on the underside of the lid as shown in block 169.

The lid is then lowered toward the specimen plate so that the alignment tabs engage sidewalls on the specimen plate, thereby facilitating the alignment of the sealing area and the sealing surface. When the lid is fully lowered and resting on the specimen plate as shown in block 173, the lid is fitted to the specimen plate. With the lid fitted to the specimen plate, the weight of the lid compresses the compliant seal against the sealing surface as shown in block 175. Thereby the specimen plate is sufficiently sealed against contamination and impermissible evaporation as shown in block 177.

Figure 21A:
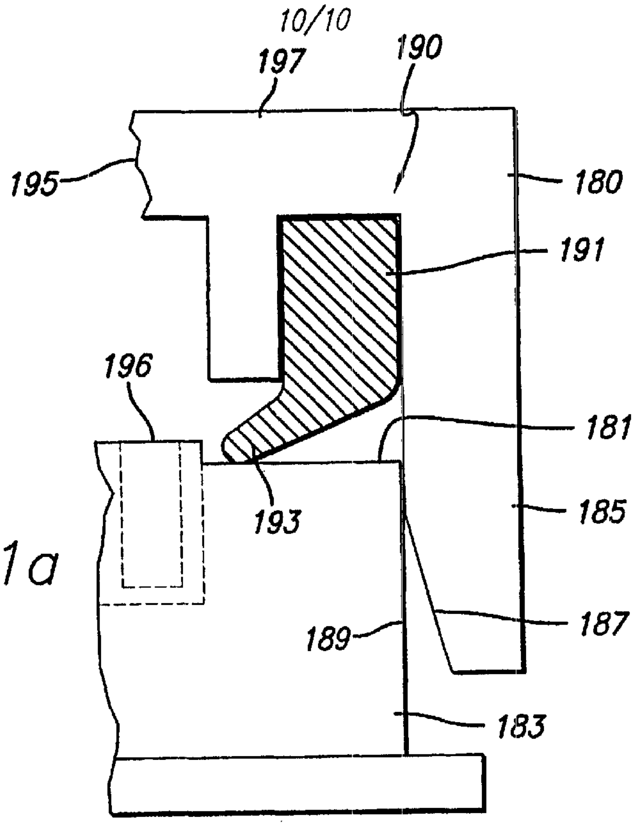
FIG. 21 is a partial cross-section view of a specimen plate lid made in accordance with the present invention.
Figure 21B:
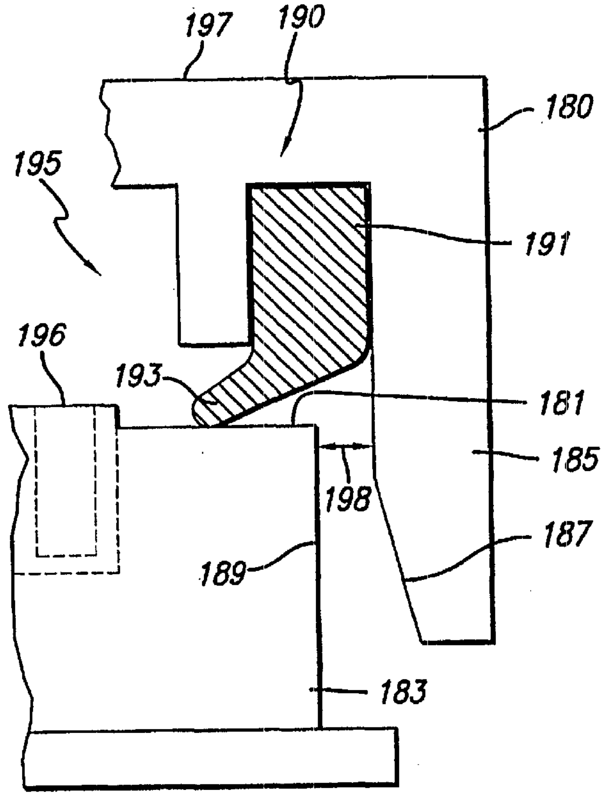

FIG. 21 shows a specimen plate lid 180 sealing the perimeter 181 of a specimen plate 183. The lid 180 has an alignment tab 185 with a chamfered surface 187 for facilitating the engagement of the sidewall 189 of the specimen plate 183. The lid 180 has a perimeter groove 190 fittingly receiving a compliant rubber seal 191. The lid 180 has sufficient weight that when resting on the plate 183, the leg 189 of the real 191 is compressed against the perimeter 181 of the plate 183. Accordingly, the internal volume 195 under the cover 197 is sealed against impermissible evaporation and contamination. The lid may be positioned such that the alignment tab 185 is positioned against the plate sidewall 189, as shown in FIG. 21*a*, or may be positioned away a distance 198 as shown in FIG. 21*b*. Either way, the seal 191 is positioned in the lid 180 so that the leg 193 of the seal 191 does not contact any sample well, such as perimeter sample well 196. In such a manner, the seal avoids contaminating any sample well and facilitates reduced edge effects and more even gas diffusion.

One skilled in the art will appreciate that the present invention can be practiced by other than the preferred embodiments which are presented in this description for purposes of illustration and not of limitation, and the present invention is limited only by the claims which follow. It is noted that equivalents for the particular embodiments discussed in this description may practice the invention as well.

What is claimed is:

1. A lid for a specimen plate, the lid comprising:

a cover having a top surface, a bottom surface, and a side;

an alignment protrusion extending from the side of the cover, the alignment protrusion positioned to cooperate with an alignment member of a specimen plate, wherein the alignment protrusion is a plurality of alignment tabs, wherein the alignment protrusion does not mechanically mate with the specimen plate or frictionally mate with sidewalls of the specimen plate when the lid is placed on the specimen plate; and a sealing perimeter positioned on the bottom surface of the cover;

wherein the alignment protrusion facilitates aligning the lid to a specimen plate so that a seal is compressibly received between the sealing perimeter and a sealing surface of a specimen plate when the lid is placed on the specimen plate.

2. The lid according to claim 1 wherein the alignment member of the specimen plate includes at least one sidewall of the specimen plate.

3. The lid according to claim 1 wherein the seal is a perimeter seal attached to the sealing perimeter.

4. The lid according to claim 1 wherein the lid is constructed from a single block.

5. The lid according to claim 1 wherein the lid is constructed of a heavy material to facilitate compressing the seal.

6. The lid according to claim 1 wherein the lid is constructed from stainless steel.

7. The lid according to claim 1 wherein the cover has separate weight members attached to the cover.

8. The lid according to claim 1 wherein the cover has a weight in the range of about 100 grams to about 500 grams to facilitate compressing the seal.

9. The lid according to claim 1 wherein the cover has a weight of about 400 grams to facilitate compressing the seal.

10. The lid according to claim 1 wherein the alignment protrusion is constructed within a tolerance of about 0.100 mm to about 0.2 mm.

11. The lid according to claim 1 wherein the seal is a contiguous perimeter seal between the lid and specimen plate.

12. The lid according to claim 1 wherein the cover is substantially rectangular, with a longer edge and a shorter edge, and the alignment member are sidewalls of the specimen plate.

13. The lid according to claim 12 wherein at least one alignment tab is positioned along each, shorter edge and at least one alignment tab is positioned along each longer edge.

14. The lid according to claim 13 wherein two alignment tabs are positioned near the ends of each shorter edge and a single alignment tab is positioned near the center of each longer edge.

15. The lid according to claim 1 wherein the seal extends around a corner of the cover by using two connected forty-five degree angles.

16. The lid according to claim 1 wherein the alignment tabs are constructed in the form of at least two corner tabs.

17. The lid according to claim 1 wherein the seal fits into a groove.

18. The lid according to claim 1 wherein the seal is a perimeter seal constructed of a compliant material.

19. The lid according to claim 18 wherein the perimeter seal is constructed of a silicone rubber.

20. The lid according to claim 1 wherein the cover has a plurality of through-holes for diffusing gas, the through-holes positioned within an area bounded by the sealing perimeter.

21. The lid according to claim 20 wherein each through-hole is about 1 mm in diameter.

22. The lid according to claim 1 wherein the lid further includes a recessed area for increasing a volume of gas retained between the cover and a top surface of the specimen plate.

23. The lid according to claim 22 wherein the lid further includes through-holes positioned in an area bounded by the sealing perimeter, the through-holes constructed to keep the volume of retained gas at an approximately 5 percent $CO_2$ concentration.

24. The lid according to claim 1 wherein the lid further includes an opening having a gas permeable membrane for diffusing.

25. The lid according to claim 1 wherein the lid further includes a gripper structure for coupling with a robotic gripper.

26. The lid according to claim 25 wherein the gripper structure includes a gripper lip positioned at an edge of the cover.

27. The lid according to claim 1 wherein the alignment protrusion has a chamfer at a lower portion cooperating with the sidewall.

28. The lid according to claim 1, wherein the lid comprises a bar code.

29. The lid according to claim 28, wherein the bar code is positioned at one end of the lid.

30. The lid according to claim 28, wherein the lid comprises two or more bar codes.

31. The lid according to claim 30, wherein one bar code is positioned at each end of the lid.

32. The lid according to claim 1, wherein the lid comprises a robotic gripper that can lift the lid from a specimen plate and position the lid on a specimen plate.

33. The lid according to claim 1, wherein the lid lacks a mechanical or adhesive sealing mechanism.

34. A lid for a specimen plate, the lid comprising:

a cover having a top surface, a bottom surface, and a side;

an alignment protrusion extending from the side of the cover, the alignment protrusion positioned to precisely cooperate with a sidewall of a specimen plate, wherein the alignment protrusion does not mechanically mate with the specimen plate or frictionally mate with sidewalls of the specimen plate when the lid is placed on the specimen plate; and a sealing perimeter on the bottom surface of the cover;

wherein the alignment protrusion facilitates aligning the sealing perimeter to a sealing area on the plate, the cover being precisely positioned so that the sealing perimeter does not touch any sample well on a specimen plate when the lid is placed on the specimen plate.

* * * * *